US008772563B2

(12) United States Patent
Lauritzen et al.

(10) Patent No.: US 8,772,563 B2
(45) Date of Patent: Jul. 8, 2014

(54) PROCESS FOR THE CONVERSION OF ETHANE TO AROMATIC HYDROCARBONS

(75) Inventors: Ann Marie Lauritzen, Houston, TX (US); Ajay Madhav Madgavkar, Katy, TX (US)

(73) Assignee: Shell Oil Company, Houston, TX (US)

( * ) Notice: Subject to any disclaimer, the term of this patent is extended or adjusted under 35 U.S.C. 154(b) by 651 days.

(21) Appl. No.: 12/371,803

(22) Filed: Feb. 16, 2009

(65) Prior Publication Data
US 2009/0209794 A1 Aug. 20, 2009

Related U.S. Application Data

(60) Provisional application No. 61/029,478, filed on Feb. 18, 2008.

(51) Int. Cl.
C07C 2/12 (2006.01)
(52) U.S. Cl.
USPC ........... 585/415; 585/407; 585/417; 585/418; 585/419
(58) Field of Classification Search
USPC .......................... 585/407, 415, 417, 418, 419
See application file for complete search history.

(56) References Cited

U.S. PATENT DOCUMENTS

| 3,827,867 A | 8/1974 | Heinemann et al. | |
| 4,058,452 A | 11/1977 | Loboda | 208/134 |
| 4,100,218 A | 7/1978 | Chen et al. | 260/673 |
| 4,120,910 A | 10/1978 | Chu | 260/673 |
| 4,158,026 A | 6/1979 | Addison | 585/321 |
| 4,215,231 A | 7/1980 | Raymond | 585/251 |
| 4,229,602 A | 10/1980 | Brinkmeyer et al. | 585/407 |
| 4,350,835 A | 9/1982 | Chester et al. | |
| 4,528,412 A | 7/1985 | Steacy | 585/415 |
| 4,547,205 A | 10/1985 | Steacy | 55/25 |
| 4,642,402 A | 2/1987 | Jensen | 585/411 |
| 4,677,235 A | 6/1987 | Mowry | 585/415 |
| 4,766,265 A | 8/1988 | Desmond et al. | 585/415 |
| 4,806,699 A | 2/1989 | Smith et al. | 585/314 |
| 4,806,700 A | 2/1989 | Martindale | 585/322 |
| 4,855,522 A | 8/1989 | Diaz | 585/417 |
| 4,968,401 A | 11/1990 | Harandi et al. | 208/49 |
| 4,996,381 A | 2/1991 | Pickering, Jr. et al. | 585/413 |
| 5,013,423 A | 5/1991 | Chen et al. | 208/64 |
| 5,019,663 A | 5/1991 | Chou et al. | 585/415 |
| 5,026,937 A | 6/1991 | Bricker | 585/415 |
| 5,030,782 A | 7/1991 | Harandi et al. | 585/322 |
| 5,053,570 A | 10/1991 | Soto et al. | 585/417 |
| 5,186,908 A | 2/1993 | Nemet-Mavrodin et al. | 422/190 |
| 5,210,350 A | 5/1993 | Solofo et al. | |
| 5,215,950 A | 6/1993 | Bournonville et al. | 502/66 |
| 5,227,557 A | 7/1993 | Bournonville et al. | 585/419 |
| 5,258,563 A | 11/1993 | Gosling et al. | 585/322 |
| 5,386,071 A | 1/1995 | Kuchar et al. | 585/313 |
| 5,456,822 A | 10/1995 | Marcilly et al. | 208/136 |
| 5,932,777 A | 8/1999 | Sughrue, II et al. | 585/322 |
| 5,936,135 A | 8/1999 | Choudhary et al. | 585/418 |
| 6,143,941 A | 11/2000 | Sharma et al. | 585/481 |
| 6,635,792 B2 | 10/2003 | Choi et al. | 585/489 |
| 7,019,184 B2 | 3/2006 | Allison et al. | 585/415 |
| 7,186,871 B2 | 3/2007 | Mitchell et al. | 585/418 |
| 2003/0036670 A1 | 2/2003 | Oh et al. | 585/400 |
| 2004/0020827 A1* | 2/2004 | Elomari | 208/111.01 |
| 2004/0028584 A1 | 2/2004 | Juttu et al. | 423/64 |
| 2005/0143610 A1 | 6/2005 | Mitchell et al. | 585/418 |
| 2006/0287564 A1 | 12/2006 | Choi et al. | 585/489 |
| 2008/0293980 A1 | 11/2008 | Kiesslich et al. | |

FOREIGN PATENT DOCUMENTS

| CA | 2620480 | 4/2007 | C07C 2/76 |
| CN | 1070847 | 4/1993 | B01J 29/06 |
| CN | 88103549 | 12/1998 | |
| EP | 0050021 | 4/1982 | C07C 2/76 |
| EP | 0147111 | 3/1985 | C01C 2/76 |
| EP | 0244162 | 11/1987 | C07C 2/76 |
| EP | 0269297 | 11/1987 | C07C 15/00 |
| EP | 0269297 | 3/1991 | |
| EP | 0493040 | 12/1991 | C10G 35/06 |
| EP | 0512912 | 11/1992 | C07C 15/00 |
| EP | 0905112 | 3/1999 | C07C 15/46 |
| EP | 1001001 | 5/2000 | C10G 57/02 |
| GB | 1442850 | 7/1976 | C07C 3/00 |
| WO | 2004025767 | 3/2004 | |
| WO | 2004076346 | 9/2004 | |
| WO | WO2007037866 | 4/2007 | B01J 29/06 |
| WO | WO2007048853 | 5/2007 | C07C 2/84 |
| WO | 2007117406 | 10/2007 | |
| WO | WO2007144324 | 12/2007 | C07C 2/76 |
| WO | WO2009105391 | 8/2009 | C07C 2/76 |

OTHER PUBLICATIONS

F. Solymosi et al., "Conversion of ethane into benzene on $Mo_2C$/ZSM-5 catalyst," Applied Catalysis A: General, Elsevier Science, Amsterdam, NL, vol. 166, No. 1, Jan. 2, 1998 pp. 225-235, XP023613553.
Tomoyuki, Inui, Fumio Okazumi, Yoshinori Markino, "Synthesis of aromatic hydrocarbons from low-grade paraffins using high-silica zeolite catalysts and metal carriers," Chemistry Express vol. 1, No. 1, pp. 53-36, 1986.
V. R. Choudhary et al., "Effective Low-Temperature Aromatization of Ethane over H-Galloaluminosilicate (MFI) Zeolites in the Presence of Higher Alkanes or Olefins," Angew Chem. Intl. Ed. Engl. 36, No. 12 (1997) pp. 1305-1308.
Inui, T. et al. "Synthesis of Aromatic Hydrocarbons from Low-Grade Paraffins Using High-Silica Zeolite Catalysts and Metal Carriers", Chemistry Express vol. 1., pp. 53-56 (1986), Kinki Chemical Society, Japan.
Hagen A., et al., "Synthesis of Iron-Containing MFI Type Zeolites and its Application to the Conversion of Ethane Into Aromatic Compounds", Zeolites, vol. 15, pp. 270-275 (995) Elsevier Science Inc. 1995.

(Continued)

Primary Examiner — Elizabeth Wood

(57) ABSTRACT

A process for producing aromatic hydrocarbons which comprises (a) contacting ethane with a dehyroaromatization aromatic catalyst which is comprised of about 0.005 to about 0.1 wt % platinum, an amount of gallium which is equal to or greater than the amount of the platinum, from about 10 to about 99.9 wt % of an aluminosilicate, and a binder, and (b) separating methane, hydrogen, and $C_{2-5}$ hydrocarbons from the reaction products of step (a) to produce aromatic reaction products including benzene.

19 Claims, No Drawings

(56) References Cited

OTHER PUBLICATIONS

Waku T., et al., Catalytic Dehydrogenation of Alkanes on Pt/Na-[Fe]ZSM5 and Staged O2 Introduction for Selective H2 Removal, Journal of Catalysis, vol. 222, (2004), pp. 481-492.

Oygarden, A H., et al., "Activity of Commercial Zeolites with Iron Impurities in Direct N20 Decomposition", Applied Catalysis B:Environmenta, vol. 65 (2006), pp. 163-167.

Querini C.A., Encyclopedia of Catalysis, "Reforming Heterogeneous", vol. 6, pp. 1-56, I.T. Horvath, ed., published by John Wiley & Sons, Inc. Hoboken, NJ, USA, (2003).

* cited by examiner

PROCESS FOR THE CONVERSION OF ETHANE TO AROMATIC HYDROCARBONS

CROSS REFERENCE TO RELATED APPLICATION

This application claims priority to U.S. Provisional Application Ser. No. 61/029,478 filed Feb. 18, 2008, the entire disclosure of which is hereby incorporated by reference.

FIELD OF THE INVENTION

The present invention relates to a process for producing aromatic hydrocarbons from ethane. More specifically, the invention relates to a dehydroaromatization process for increasing the production of benzene and/or total aromatics from ethane.

BACKGROUND OF THE INVENTION

There is a projected global shortage for benzene which is needed in the manufacture of key petrochemicals such as styrene, phenol, nylon and polyurethanes, among others. Generally, benzene and other aromatic hydrocarbons are obtained by separating a feedstock fraction which is rich in aromatic compounds, such as reformates produced through a catalytic reforming process and pyrolysis gasolines produced through a naphtha cracking process, from non-aromatic hydrocarbons using a solvent extraction process.

In an effort to meet growing world demand for benzene and other aromatics, various industrial and academic researchers have been working for several decades to develop catalysts and processes to make light aromatics (benzene, toluene, xylenes, or BTX) from cost-advantaged, light paraffin ($C_1$-$C_4$) feeds. Prior-art catalysts devised for this application usually contain an acidic zeolite material such as ZSM-5 and one or more metals such as Pt, Ga, Zn, Mo, etc. to provide a dehydrogenation function. For example, U.S. Pat. No. 7,186,871 describes a process for lower alkane aromatization utilizing a Pt/ZSM-5 catalyst. In this patent, data are presented for propane aromatization over various Pt/ZSM-5 catalysts, with the results showing better activity and selectivity to BTX as the Pt level of the catalyst is increased from 0.06 to 0.33% wt. As another example, U.S. Pat. No. 4,350,835 covers a process for producing aromatic compounds from ethane-containing feed using a Ga-containing zeolitic catalyst which may be of the ZSM-5 type. This latter patent teaches that the Ga content of the catalyst may vary between 0.05 and 10% wt, preferably between 0.5 and 5% wt.

Aromatization of ethane and other lower alkanes is thermodynamically favored at high temperature and low pressure without addition of hydrogen to the feed. Unfortunately, these process conditions are also favorable for rapid catalyst deactivation due to formation of undesirable surface coke deposits which block access to the active sites.

For many hydrocarbon processing applications, one approach to reducing catalyst performance decline rates due to coking is to increase the catalyst metals loading in an effort to promote faster hydrogenation/breakup of large coke precursor molecules on the surface. Another approach involves incorporation of additives such as phosphate or rare earths to moderate surface acidity and reduce coking rates under reaction conditions. These approaches are appropriate for processes featuring fixed or slowly-moving catalyst beds wherein the average catalyst particle residence time in the reactor zone between regenerations (coke burnoff steps) is relatively long (at least several days). For example, see U.S. Pat. Nos. 4,855,522 and 5,026,937, which describe ZSM-5-type lower-alkane aromatization catalysts promoted with Ga and additionally containing either a rare earth metal or a phosphorus-containing alumina, respectively.

Yet another approach to circumvent this problem is to devise a lower alkane aromatization process in which the catalyst spends a relatively short time (less than a day) under reaction conditions before being subjected to coke burnoff and/or other treatment(s) aimed at restoring all or some of the original catalytic activity. An example of such a process is one featuring two or more parallel reactors containing fixed or stationary catalyst beds, with at least one reactor offline for catalyst regeneration at any given time, while the other reactor(s) is/are processing the lower alkane feed under aromatization conditions to make aromatics. Another example of such a process features a fluidized catalyst bed, in which catalyst particles cycle rapidly and continuously between a reaction zone where aromatization takes place and a regeneration zone where the accumulated coke is burned off the catalyst to restore activity. For example, U.S. Pat. No. 5,053,570 describes a fluid-bed process for converting lower paraffin mixtures to aromatics.

Requirements for optimal catalyst performance in a process involving a relatively short period of catalyst exposure to reaction conditions between each regeneration treatment, such as a fluidized-bed process, can differ from those of fixed- or moving-bed processes which require longer catalyst exposure time to reaction conditions between regeneration treatments. Specifically, in processes involving short catalyst exposure times, it is important that the catalyst not exhibit excessive initial cracking or hydrogenolysis activity which could convert too much of the feedstock to undesirable, less-valuable byproducts such as methane.

Certain metals such as Pt which are very suitable for catalyzing the dehydrogenation reactions needed for aromatization can also, under certain circumstances, display undesirable hydrogenolysis activity that leads to excessive production of methane from higher hydrocarbons. The inclusion of a second, inert or less-active metal in a catalyst composition to help suppress the hydrogenolysis activity of the first, more-active metal is used in commercial scale catalytic naphtha reforming in which $C_5$-$C_{12}$ paraffins and naphthenes are converted to aromatic compounds with catalysts which are predominantly bimetallic and are supported on chloride-promoted alumina. As indicated in a catalytic naphtha reforming review article by C. A. Querini in volume 6, pages 1-56 of the *Encyclopedia of Catalysis* (I. T. Horvath, ed.; published by John Wiley & Sons, Inc., Hoboken, N.J., USA, 2003), these catalysts typically contain Pt plus another metal such as Re (in sulfided form) or Sn. Among other effects, these second metals can interact with the Pt to reduce hydrogenolysis activity, thereby decreasing the rate of unwanted methane formation.

These Pt/Re and Pt/Sn catalysts, supported on chloride-promoted alumina, are widely employed in fixed-bed (semi-regenerative) and moving-bed (continuous) naphtha reformers, respectively, and their compositions are optimized for relatively long catalyst exposure times to reaction conditions between regeneration treatments. The average catalyst particle residence time in the reaction zone between regeneration treatments ranges from a few days in moving bed reactors and up to 1 or 2 years in fixed bed reactors. According to the article by Querini mentioned above, typical Pt and Sn levels in Pt/Sn naphtha reforming catalysts are about 0.3% wt each. Such catalysts, which usually lack a strongly acidic zeolite component, do not work well for lower alkane aromatization.

It would be advantageous to provide a light hydrocarbon dehydroaromatization process which can be performed under conditions thermodynamically favorable for light alkane aromatization as described above, which provides for relatively short catalyst exposure time to reaction conditions, wherein the average catalyst particle residence time in the reaction zone between regeneration treatments may be from about 0.1 second to about 30 minutes in a fluidized bed reactor and from a few hours up to a week in moving bed and fixed bed reactors, and in which the catalyst composition is optimized to reduce excessive initial production of less-desirable byproducts such as methane.

SUMMARY OF THE INVENTION

The present invention provides a process for producing aromatic hydrocarbons which comprises:

(a) contacting ethane with a dehydroaromatization catalyst wherein the ethane contact time (the average residence time of a given ethane molecule in the reaction zone under reaction conditions) is preferably from about 0.1 seconds to about 1 minute, most preferably about 1 to about 5 seconds, preferably at about 550 to about 730° C. and about 0.01 to about 1.0 MPa, said catalyst comprising:
  (1) about 0.005 to about 0.1 wt % (% by weight) platinum, basis the metal, preferably about 0.01 to about 0.05% wt, most preferably about 0.02 to about 0.05% wt,
  (2) an amount of gallium which is equal to or greater than the amount of the platinum, preferably no more than about 1 wt %, most preferably no more than about 0.5 wt %;
  (3) about 10 to about 99.9 wt % of an aluminosilicate, preferably a zeolite, basis the aluminosilicate, preferably about 30 to about 99.9 wt %, preferably selected from the group consisting of ZSM-5, ZSM-11, ZSM-12, ZSM-23, or ZSM-35, preferably converted to the H+ form, preferably having a $SiO_2/Al_2O_3$ molar ratio of from about 20:1 to about 80:1, and
  (4) a binder, preferably selected from silica, alumina and mixtures thereof;

(b) collecting the products from (a) and separating and recovering $C_{6+}$ aromatic hydrocarbons;

(c) optionally recovering methane and hydrogen; and (d) optionally recycling $C_{2-5}$ hydrocarbons to (a).

The reactor system may comprise one or more reaction vessels, chambers, or zones, arranged in parallel or in series, in which contact between the catalyst particles and the ethane-containing feed occurs. The reactor vessel(s), chamber(s), or zone(s) may feature a fixed catalyst bed (i.e., with parallel beds), a slowly-moving catalyst bed, or a fluidized bed, In a preferred embodiment, a fluidized-bed reactor is used. The process is optimized to minimize the average catalyst particle residence time while maintaining selectivity and conversion rate. The average catalyst particle residence time is the average amount of time that a catalyst particle is in the active reaction zone with ethane between regenerations.

Catalysts of the present invention—featuring lower levels of a strong dehydrogenation metal (preferably Pt) with a potentially strong cracking activity, complemented with gallium, which has lesser dehydrogenation activity than Pt but can also suppress undesired cracking reactions—are designed to limit initial cracking activity without sacrificing the overall activity and aromatics selectivity required for commercially-viable production rates of benzene and other aromatics.

DETAILED DESCRIPTION OF THE INVENTION

The present invention is a process for producing aromatic hydrocarbons which comprises bringing a hydrocarbon feedstock containing at least about 50 percent by weight of ethane or other $C_2$ hydrocarbons into contact with a dehydroaromatization catalyst composition suitable for promoting the reaction of ethane to aromatic hydrocarbons such as benzene at a temperature of about 550 to about 730° C. and a pressure of about 0.01 to about 1.0 MPa. The primary desired products of the process of this invention are benzene, toluene and xylene.

The hydrocarbons in the feedstock may be ethane, ethylene or mixtures thereof. Preferably, the majority of the feedstock is ethane and from about 0 to about 20 weight percent of the feedstock may be comprised of ethylene, preferably about 5 to about 10 weight percent. The feedstock may contain in addition up to about 40 weight percent of other open chain hydrocarbons containing between 3 and 8 carbon atoms as coreactants. Specific examples of such additional coreactants are propane, propylene, n-butane, isobutane, n-butenes and isobutene. The hydrocarbon feedstock preferably contains at least about 60 percent by weight of $C_2$ hydrocarbons, more preferably at least about 70 percent by weight. The reaction feed is often referred to herein as ethane for convenience but it is meant to include all of the other hydrocarbon materials referred to above if it is necessary or desired for them to be present.

In a preferred embodiment, the reactor comprises a zone, vessel, or chamber containing catalyst particles through which the ethane-containing feed flows and the reaction takes place. The reactor system may involve a fixed, moving, or fluidized catalyst bed. The reaction products then flow out of the bed and are collected. The reaction products are then separated and $C_{6+}$ aromatic hydrocarbons are recovered. Optionally, methane and hydrogen are recovered and optionally the $C_{2-5}$ hydrocarbons are recycled to step (a).

A fixed bed reactor is a reactor in which the catalyst remains stationary in the reactor and the catalyst particles are arranged in a vessel, generally a vertical cylinder, with the reactants and products passing through the stationary bed. In a fixed bed reactor the catalyst particles are held in place and do not move with respect to a fixed reference frame. The fixed bed reactor may be an adiabatic single bed, a multi-tube surrounded with heat exchange fluid or an adiabatic multi-bed with internal heat exchange, among others. Fixed bed reactors are also referred to as packed bed reactors. Fixed bed reactors provide excellent gas solids contacting. The fixed bed reactor configuration may include at least two separate fixed beds in different zones so that at least one bed can be in active operation under reaction conditions while the catalyst the other bed(s) is being regenerated.

In a moving bed catalytic reactor, gravity causes the catalyst particles to flow while maintaining their relative positions to one another. The bed moves with respect to the wall of the vessel in which it is contained. The reactants may move through this bed with cocurrent, countercurrent or crossflow. Plug flow is the preferred mode. The moving bed offers the ability to withdraw catalyst particles continuously or intermittently so they can be regenerated outside the reactor and reintroduced into the circuit later on. Thus, there is an advantage to using a moving bed when the catalyst has a short active life and can be continuously regenerated. A moving bed reactor may consist of at least one tray as well as supporting means for one or more catalyst beds. The supporting means may be permeable to gas and impermeable to catalyst particles.

A fluidized bed reactor is a type of reactor that may be used to carry out a variety of multiphase chemical reactions. In this type of a reactor, a gas is passed through the particulate catalyst at high enough velocities to suspend the solid and cause it to behave as though it were a fluid. The catalyst particles may be supported by a porous plate. The gas may be forced through the porous plate up through the solid material. At lower gas velocities the solids remain in place as the gas passes through the voids in the material. As the gas velocity is increased, the reactor reaches the stage where the force of the fluid on the solids is enough to balance the weight of the solid material and above this velocity the contents of the reactor bed begin to expand and swirl around much like an agitated tank or boiling pot of water. A fluidized bed reactor is preferred for use in the present invention because it provides uniform particle mixing, uniform temperature gradients and the ability to operate the reactor in a continuous state. The catalyst leaves the reaction zone with the reaction products and is separated therefrom in order to be regenerated before being recycled to the reaction zone.

The ethane contact time may range from about 0.1 second to about 1 minute. The ethane contact time is the average amount of time that one molecule of the ethane feed is in the reaction zone. The preferred ethane contact time is from about 1 to about 5 seconds. Longer ethane contact times are less desirable because they tend to allow for secondary reactions that lead to less-desirable byproducts such as methane and reduce selectivity to benzene and/or total aromatics.

The catalyst comprises from about 0.005 to about 0.1 wt % platinum, basis the metal. The platinum is highly active in terms of catalyzing the dehydroaromatization reaction and it is best if its concentration in the catalyst not be more than 0.1 wt % because otherwise too much methane will be produced. In one embodiment from about 0.01 to about 0.05 wt % platinum is used, preferably from about 0.02 to about 0.05 wt % of platinum is used. High performance is thus obtained with relatively low amounts of metals in the catalyst.

A second metal, namely gallium (Ga), is an essential component of the catalyst of the present invention. The Ga helps to suppress undesirable catalytic activity which leads to the production of less-valuable methane byproduct, leading to an improvement in selectivity to benzene and total aromatics without excessively dampening the total level of ethane conversion or aromatics production. For the present invention, the amount of Ga, by weight, in the catalyst composition may be equal to or greater than the amount of Pt, basis the metal. In one embodiment no more than about 1 wt % of gallium may be used. Preferably no more than about 0.5 wt %, most preferably no more than about 0.3 wt %, is used.

The catalyst also comprises from about 10 to about 99.9 wt % of one or more aluminosilicate materials, preferably from about 30 to about 99.9 wt %, basis the aluminosilicate(s). The aluminosilicates preferably have a silicon dioxide:aluminum trioxide molar ratio of from about 20 to about 80. The aluminosilicates may preferably be zeolites having the MFI or MEL type structure and may be ZSM-5, ZSM-8, ZSM-11, ZSM-12 or ZSM-35. The zeolite or zeolite mixture is preferably converted to $H^+$ form to provide sufficient acidity to help catalyze the dehydroaromatization reaction. This can be accomplished by calcining the ammonium form of the zeolite in air at a temperature of at least about 400° C.

The binder material serves the purpose of holding individual zeolite crystal particles together to maintain an overall catalyst particle size in the optimal range for fluidized-bed operation or to prevent excessive pressure drop in fixed or moving bed operation. The binder may be selected from the group consisting of alumina, silica, silica/alumina, various clay materials such as kaolin, or mixtures thereof. Preferably, amorphous inorganic oxides of gamma alumina, silica, silica/alumina or a mixture thereof may be included. Most preferably, alumina and/or silica are used as the binder material.

A platinum containing crystalline aluminosilicate, such as ZSM-5, may be synthesized by preparing the aluminosilicate containing the aluminum and silicon in the framework, depositing platinum on the aluminosilicate and then calcining the aluminosilicate. The gallium may also be added by the same procedure, either prior to, simultaneously with, or after the addition of platinum. The metals may be added by any commonly known method for adding metals to such structures including incorporation into the aluminosilicate framework during crystal synthesis, or subsequent ion exchange into an already-synthesized crystal framework, or well as by various impregnation methods known to those skilled in the art. The platinum and gallium may be added by the same or different methods.

In a preferred embodiment of the present invention an ethane feedstream is introduced into the dehydroaromatization reactor. The feedstream then comes into contact with the catalyst particles for the prescribed period of time. The reaction products leave the reactor and are transferred into a separator. The separator removes the aromatic products and the principal byproducts, methane and hydrogen, which preferably may be recovered, and also removes $C_{2-5}$ byproducts and unreacted ethane which optionally may be recycled to the dehydroaromatization reactor.

EXAMPLES

The following example is illustrative only and is not intended to limit the scope of the invention.

Example 1

Catalysts A through H were prepared on samples of an extrudate material containing 80% wt of CBV 3014E ZSM-5 zeolite (30:1 molar $SiO_2:Al_2O_3$ ratio, available from Zeolyst International) and 20% wt of alumina binder. The extrudate samples were calcined in air up to 425° C. to remove residual moisture prior to use in catalyst preparation.

Metals were deposited on 25-50 gram samples of the above ZSM-5/alumina extrudate by first combining appropriate amounts of stock solutions of tetraammine platinum nitrate and gallium(III) nitrate, diluting this mixture with deionized water to a volume just sufficient to fill the pores of the extrudate, and impregnating the extrudate with this solution at room temperature and atmospheric pressure. Impregnated samples were aged at room temperature for 2-3 hours and then dried overnight at 100° C.

To determine the platinum and gallium contents of each catalyst, a sample of the catalyst was calcined at 550° C. to drive off residual moisture to render a loss on ignition (LOI) percentage. A known mass of the untreated ground catalyst, corrected by LOI percentage, was digested using closed vessel microwave acid digestion involving nitric, hydrochloric, and hydrofluoric acids. The solution was diluted to a known volume with deionized water and then analyzed for the indicated metals by directly coupled plasma emission analysis. Results are reported as ppmw or weight percent based on the weight of the 550° C.-calcined catalyst sample.

Catalysts made on the ZSM-5/alumina extrudate were tested "as is," without crushing. For each performance test, a 15-cc charge of catalyst was loaded into a quartz tube (1.40 cm i.d.) and positioned in a three-zone furnace connected to an automated gas flow system.

Prior to performance testing, all catalyst charges were pretreated in situ at atmospheric pressure as follows:

(a) calcination with air at 60 liters per hour (L/hr), during which the reactor wall temperature was increased from 25 to 510° C. in 12 hrs, held at 510° C. for 4-8 hrs, then further increased from 510 to 630° C. in 1 hr, then held at 630° C. for 30 min;

(b) nitrogen purge at 60 L/hr, 630° C. for 20 min;

(c) reduction with hydrogen at 60 L/hr, 630° C. for 30 min.

At the end of the pretreatment, 100% ethane feed was introduced at 15 L/hr (1000 gas hourly space velocity-GHSV), atmospheric pressure, with the reactor wall temperature maintained at 630° C. The total reactor outlet stream was sampled and analyzed by an online gas chromatography system two minutes after ethane feed addition. Based on composition data obtained from the gas chromatographic analysis, initial ethane conversion and hydrocarbon product selectivities were computed according to the following formulas:

ethane conversion, %=100×(100−% wt ethane in outlet stream)/(% wt ethane in feed)

selectivity to hydrocarbon product Y (other than ethane)=100×(moles of carbon in amount of product Y generated)/(moles of carbon in amount of ethane reacted)

For purposes of the selectivity calculation, $C_{9+}$ aromatics were assumed to have an average molecular formula of $C_{10}H_8$ (naphthalene).

The analyzed platinum and gallium levels and initial aromatization performance data for Catalysts A-H, prepared and tested as described above, are presented in Table 1. The data in Table 1 indicate that the low-Pt/Ga/ZSM-5 catalysts B through F of the present invention provide better initial suppression of methane production and higher selectivity to benzene and total aromatics under ethane aromatization conditions than catalysts A, G, and H, in which the Pt and/or Ga levels fall outside the ranges of the present invention.

TABLE 1

| Catalyst | A | B | C | D | E | F | G | H |
|---|---|---|---|---|---|---|---|---|
| Analyzed Pt Level, % wt | 0.018 | 0.024 | 0.022 | 0.024 | 0.0275 | 0.028 | 0.198 | 0.213 |
| Analyzed Ga Level, % wt | 0.014 | 0.025 | 0.092 | 0.150 | 0.472 | 0.912 | 0.145 | 0.917 |
| Ethane conversion, % | 44.88 | 43.95 | 43.5 | 46.49 | 48.25 | 46.93 | 63.24 | 50.04 |
| Selectivities, % (carbon basis) | | | | | | | | |
| Methane | 26.45 | 18.43 | 16.95 | 17.78 | 16.08 | 18.1 | 42.65 | 22.50 |
| Ethylene | 12.79 | 12.25 | 10.15 | 12.30 | 10.82 | 11.16 | 8.2 | 9.98 |
| Propylene | 1.84 | 1.74 | 1.48 | 1.57 | 1.39 | 1.44 | 0.64 | 1.14 |
| Propane | 1.65 | 1.85 | 1.97 | 1.57 | 1.46 | 1.54 | 0.5 | 1.24 |
| C4 Hydrocarbons | 0.36 | 0.37 | 0.35 | 0.35 | 0.34 | 0.30 | 0.16 | 0.26 |
| C5 Hydrocarbons | 0.01 | 0.03 | 0.04 | 0.03 | 0.01 | 0.01 | 0.01 | 0.01 |
| Benzene | 34.21 | 38.13 | 37.09 | 38.54 | 36.02 | 36.76 | 30.41 | 36.47 |
| Toluene | 17.64 | 19.74 | 19.89 | 19.43 | 17.86 | 17.82 | 13.11 | 16.93 |
| C8 Aromatics | 3.16 | 3.42 | 4.05 | 3.33 | 3.37 | 2.76 | 2.03 | 2.55 |
| C9+ Aromatics | 1.90 | 4.04 | 8.05 | 5.09 | 12.64 | 10.11 | 2.3 | 8.94 |
| Total Aromatics | 56.91 | 65.33 | 69.07 | 66.39 | 69.89 | 67.45 | 47.85 | 64.88 |

What is claimed is:

1. A process for producing aromatic hydrocarbons which comprises:
   (a) contacting ethane with a dehydroaromatization catalyst which comprises:
      (1) 0.01 to 0.05 wt % platinum, based on the total weight of the catalyst calculated as metal,
      (2) an amount of gallium equal to or greater, by weight, than the amount of the platinum, basis the metal, and no more than about 1 wt %, based on the total weight of the catalyst calculated as metal;
      (3) about 10 to about 99.9 wt % of an aluminosilicate, and
      (4) a binder;
   (b) collecting the products from (a) and separating and recovering $C_{6+}$ aromatic hydrocarbons,
   (c) optionally recovering methane and hydrogen; and
   (d) optionally recycling $C_{2-5}$ hydrocarbons to (a).

2. The process of claim 1 wherein the reactor comprises a bed of catalyst particles and the ethane flows through the bed.

3. The process of claim 2 wherein the reactor is selected from fixed bed, moving bed, and fluidized bed reactors.

4. The process of claim 1 wherein the ethane contact time is from about 0.1 seconds to about 1 minute.

5. The process of claim 1 wherein the reaction is carried out at from about 550 to about 730° C. and from about 0.01 to about 1.0 MPa.

6. The process of claim 1 wherein the amount of platinum is from about 0.02 to about 0.05 wt %, based on the total weight of the catalyst calculated as metal.

7. The process of claim 1 wherein the catalyst comprises no more than about 0.5 wt % of gallium, calculated as metal.

8. The process of claim 1 wherein the amount of the aluminosilicate is from about 30 to about 99.9 wt % based on the total weight of the catalyst.

9. The process of claim 1 wherein the aluminosilicate has a silicon dioxide:aluminum trioxide molar ratio of from about 20 to about 80.

10. The process of claim 1 wherein the aluminosilicate is a zeolite.

11. The process of claim 10 wherein the zeolite is selected from the group consisting of ZSM-5, ZSM-11, ZSM-12, ZSM-23, and ZSM-35.

12. The process of claim 10 wherein the zeolite is converted to the $H^+$ form.

13. The process of claim 1 wherein the binder is selected from silica, alumina and mixtures thereof.

14. A process for producing aromatic hydrocarbons which comprises:
   (a) contacting ethane with a dehydroaromatization catalyst which comprises:
      (1) 0.005 to 0.05 wt % platinum, based on the total weight of the catalyst calculated as metal,
      (2) an amount of gallium equal to or greater, by weight, than the amount of the platinum, basis the metal, and no more than about 1 wt %, based on the total weight of the catalyst calculated as metal;

(3) about 10 to about 99.9 wt % of an aluminosilicate, and
(4) a binder;
(b) collecting the products from (a) and separating and recovering $C_{6+}$ aromatic hydrocarbons,
(c) optionally recovering methane and hydrogen; and
(d) optionally recycling $C_{2-5}$ hydrocarbons to (a).

15. The process of claim 14 wherein the reactor is selected from fixed bed, moving bed, and fluidized bed reactors.

16. The process of claim 14 wherein the ethane contact time is from about 0.1 seconds to about 1 minute.

17. The process of claim 14 wherein the reaction is carried out at from about 550 to about 730° C. and from about 0.01 to about 1.0 MPa.

18. The process of claim 14 wherein the catalyst comprises no more than about 0.5 wt % of gallium, calculated as metal.

19. The process of claim 14 wherein the amount of the aluminosilicate is from about 30 to about 99.9 wt % based on the total weight of the catalyst.

\* \* \* \* \*